(12) United States Patent
Andersson et al.

(10) Patent No.: US 7,005,071 B2
(45) Date of Patent: Feb. 28, 2006

(54) METHOD OF GENERATING METAL CHELATING AFFINITY LIGANDS

(75) Inventors: Lars C. Andersson, Uppsala (SE); Tesfai Gebru, Uppsala (SE); Andreas Axén, Uppsala (SE); Jean-Luc Maloisel, Uppsala (SE)

(73) Assignee: Amersham Biosciences AB, Uppsala (SE)

( * ) Notice: Subject to any disclaimer, the term of this patent is extended or adjusted under 35 U.S.C. 154(b) by 209 days.

(21) Appl. No.: 10/699,058

(22) Filed: Oct. 31, 2003

(65) Prior Publication Data

US 2004/0168983 A1 Sep. 2, 2004

(30) Foreign Application Priority Data

Feb. 28, 2003 (SE) .................... 0300567

(51) Int. Cl.
*B01D 15/08* (2006.01)
(52) U.S. Cl. .................. 210/635; 210/656; 210/198.2; 210/502.1; 502/401; 502/439
(58) Field of Classification Search ................ 210/635, 210/656, 659, 679, 198.2, 502.1; 502/401, 502/402, 439
See application file for complete search history.

(56) References Cited

U.S. PATENT DOCUMENTS 4,551,271 A 11/1985 Hochuli 4,877,830 A 10/1989 Dobeli et al.
6,872,317 B1 * 3/2005 Nambu et al. .............. 210/679

FOREIGN PATENT DOCUMENTS

| EP | 0 108 406 | 5/1984 |
| WO | WO94/22492 | 10/1994 |
| WO | WO94/22497 | 10/1994 |
| WO | WO01/81365 | 11/2001 |

* cited by examiner

*Primary Examiner*—Ernest G. Therkorn
(74) *Attorney, Agent, or Firm*—Royal N. Ronning, Jr.; Yonggang Ji (57) ABSTRACT

The present invention relates to a method of generating at least one polydentate metal chelating affinity ligand, which method comprises the steps of
a) providing at least one cyclic scaffold comprising a carbonyl, an adjacent sulphur and a nucleophile;
b) providing at least one polydentate metal chelating affinity ligand arm, optionally in a form wherein the metal chelating functionalities are protected, on each scaffold by derivatisation of the nucleophile of said scaffolds, while retaining the cyclic structure of the scaffold;
(c) ring-opening at the bond between the carbonyl and the sulphur of the derivatized scaffold by adding a reagent that adds one or more metal chelating affinity ligand arms to the scaffold; and, if required,
(d) deprotecting the functionalities of the ligand arm(s) provided in step (b).

In the most preferred embodiment of the method, steps (c) and (d) are performed simultaneously as one single step.

16 Claims, 5 Drawing Sheets

METHOD OF GENERATING METAL CHELATING AFFINITY LIGANDS

TECHNICAL FIELD

The present invention relates to a method of generating polydentate metal chelating affinity ligands. The invention also encompasses a method of generating a separation medium comprising such ligands, as well as such ligands and such a medium.

BACKGROUND

In any chemical or bioprocessing industry, the need to separate and purify a product from a complex mixture is a necessary and important step in the production line. Today, there exists a wide market of methods in which industry can accomplish these goals, one of which is chromatography. Chromatography is quite well suited to a variety of uses in the field of biotechnology, since it can separate complex mixtures with great precision and also is suitable for more delicate products, such as proteins, since the conditions under which it is performed are not typically severe.

One chromatography method, which is an especially sensitive separation technique and also applicable to most types of proteins, is metal chelate affinity chromatography (MCAC), also known as immobilised metal ion adsorption chromatography (IMAC). This technique is commonly used in purification schemes together with another chromatographic step, such ion exchange chromatography (IEX) and/or hydrophobic interaction chromatography (HIC).

More specifically, IMAC utilises matrices that comprises a group capable of forming a chelate with a transition metal ion, which chelate in turn is used as the ligand in chromatography to adsorb a compound from a liquid. The binding strength in IMAC is affected predominately by the species of metal ion, the pH of the buffers and the nature of the ligand used. Since the metal ions are strongly bound to the matrix, the adsorbed protein can be eluted either by lowering the pH or by competitive elution.

In general, IMAC is useful for separation of proteins or other molecules that present an affinity for the transition metal ion of the matrix. For example, proteins will bind to the matrix upon the presence of accessible histidine, cysteine and tryptophan residues, which all exhibit an affinity for the chelated metal.

With the advent of molecular biological techniques, proteins are now easily tailored or tagged with one or more histidine residues in order to increase their affinity to metal chelated ligands, and accordingly, metal chelate chromatography has more recently assumed a more important role in the purification of proteins.

Simple chelators have been suggested as ligands for IMAC, such as iminodiacetic acid (IDA). IDA, coupled to agarose supports and subsequent charged with various metals, such as $Cu^{2+}$, $Zn^{2+}$ and $Ni^{2+}$, has been used for capture of proteins and peptides and is also available as commercial resins. More specifically, U.S. Pat. No. 4,551,271 (Hochuli, assigned to Hoffmann-La Roche Inc.) discloses a metal chelate resin which comprises IDA ligands, in the purification of interferon. The resin can be defined by the following formula:

wherein Me is Ni or Cu.

The best results are obtained with this resin if the interferon has already been partially purified. The resin can according to the specification be prepared in a known manner by treating agarose with epichlorohydrin or epibromohydrin, reacting the resulting epoxide with iminoacetic acid disodium salt and converting the product into the copper or zinc salt by washing with a copper (II) or zinc solution.

More recently, EP 87109892.7 (F. Hoffmann-La Roche AG) and its equivalent U.S. Pat. No. 4,877,830 (Döbeli et al, assigned to Hoffmann-La Roche Inc.) disclosed a tetradentate chelator known as nitrilotriacetic acid (NTA) for use with metals that have six coordination sites. More specifically, the matrices can be described by the general formula:

wherein x=2–4. The disclosed matrix is prepared by reacting an amino acid compound of the formula $R-HN-(CH_2)_x-CH(NH_2)-COOH$, wherein R is an amino protecting group and x is 2, 3 or 4, with bromoacetic acid in alkaline medium and subsequently, after an intermediate purification step, cleaving off the protecting group and reacting this group with an activated matrix. Accordingly, the method of preparation involves separate steps for alkylating and deprotecting the amino acid, which steps renders the method time-consuming and hence costly. In addition, the alkylation chemistry is less efficient, and after deprotection, the product is not well defined regarding rest products from neutralisation and cleavage. Following this, the material is coupled to a solid support that carries carboxyl functionalities by forming an amide bond. However, this procedure may involve disadvantages, since the media obtained presents the immobilised desired chelating ligand as well as some unreacted carboxylic groups, thus yielding a heterogeneous media. Furthermore, mono-N-protected amino acid compounds are expensive starting materials, rendering the overall method even more costly.

Finally, WO 01/81365 (Sigma-Aldrich Co.) discloses a metal chelating composition that according to the specification is capable of forming relatively stable chelates with metal ions and exhibits an improved selectivity for polyhistidine tagged proteins. According to said WO 01/81365, the linkage between the chelator and the resin is an important parameter for the selectivity, and the linkage is a neutral ether, a thioether, a selenoether or an amide. The disclosed compositions are coupled to an insoluble carrier, such as Sepharose™ according to given examples. The chromatographic media is produced in two different ways; either by a solid phase reaction directly on to the pre-activated solid support eventually used in the chromatographic media, or by a separate in solution synthesis of the intermediate product N,N,N',N'-tetrakis (carboxymethyl)-L-cystine that is eventually coupled to the solid support.

The solid phase synthesis is carried out by adding L-cysteine to a previously epichlorhydrine activated Sepharose gel under alkaline conditions for a prolonged reaction time (18 h), followed by washings. Thereafter bromoacetic acid is added, again under alkaline conditions and a prolonged reaction time (72 h), and again followed by washings, and eventually capping of remaining free amino groups present on the gel with acetic acid anhydride.

Solid phase synthesis in this way offers poor control of the reaction and potential side reactions, and thereby yields a less homogeneous product.

The alternative route, relying on in solution phase synthesis of an intermediate product starts with addition of a large excess (40 times) of glyoxylic acid to L-cystine in an alkaline borate buffer. The intermediate product was thereafter, after pH manipulations and conductivity adjustment of the reaction mixture, purified with ion exchange chromatography to give N,N,N',N'-tetrakis (carboxymethyl)-L-cystine.

Before coupling to a solid support the N,N,N',N'-tetrakis (carboxymethyl)-L-cystine has to be reduced to N,N-bis (carboxymethyl)-L-cysteine using tris (carboxyethyl) phosphine under alkaline conditions. This material can finally be used for coupling to a pre-activated solid support forming the chromatographic media. This synthetic method is elaborate and depends on a large excess of reagents to form the desired product that is eventually purified under specific chromatographic conditions, followed by reduction as an additional synthetic step, and is thereby less suited for use in large-scale production.

Accordingly, there is still a need of improved methods for synthesis of IMAC ligands as well as of methods for the immobilisation thereof to a base matrix.

SUMMARY OF THE PRESENT INVENTION

Thus, one object of the present invention is an improved method of generating polydentate metal chelating affinity ligands for subsequent coupling to a base matrix, which method utilises cost-effective and easily available starting materials and reagents and provides high yields. This can be achieved as defined in claim 1.

Another object of the present invention is to enable a careful selection of the ligands that are immobilised onto a base matrix for use in IMAC. This can be achieved by a method of generating a separation medium comprising polydentate metal chelating affinity ligands coupled to a base matrix, wherein the coupling chemistry is well defined and easy to control.

A further object of the invention is to provide such a method, which results in a homogenous product.

Yet a further object of the invention is to provide a method as discussed above, which also allows introducing two or more functionalities, which functionalities may be of the same kind or different.

Another object of the present invention is to provide ligands for immobilised metal affinity chromatography, which ligands presents an improved handle for coupling to a base matrix and hence an improved coupling efficiency as compared to prior art ligands.

An additional object of the present invention is to provide a chromatographic medium, which in use for immobilised metal affinity chromatography (IMAC) yields a low leakage of metal ions.

Another object of the invention is to provide a method of generating a diverse library of metal chelating affinity ligands based on the same scaffold, which method can be used for ligand optimisation towards a specific application.

The objects of the invention can be achieved by one or more of the appended claims. Further objects, advantages and embodiments of the present invention will appear from the detailed description that follows.

BRIEF DESCRIPTION OF THE DRAWINGS

In FIG. 1, R denotes either hydrogen or alternatively an acid or base labile protecting group.

FIGS. 2(a) and (b) illustrate purification of Maltose Binding Protein with $(His)_6$-tail (MBP-His) using IMAC separation medium prepared according to the invention. More specifically, FIG. 2(a) is the chromatogram, while FIG. 2(b) is an enlargement of the gradient part of said chromatogram. In FIG. 2, the curve at A280 nm is denoted A, the percentage (%) of elution buffer is denoted B and the conductivity is denoted C.

DEFINITIONS

The term "separation medium" is used herein for a material useful e.g. as packing of a chromatography column, and more specifically consists of one or more ligands coupled to a base matrix. Thus, the base matrix acts as a carrier, while the ligands provide functionalities that interact with target substances in chromatography.

The term "spacer" is used for a chemical entity that distances a ligand from the base matrix.

The term "ligand" means herein a chemical entity capable of binding target substances. Such target substances may be either a compound, which it is desired to isolate or remove by chromatography, or alternatively an analytical target substance.

The term "polydentate metal chelating" ligands refers to ligands with two or more donor atoms that can coordinate to, i.e. chelate, a metal simultaneously. Thus, a polydentate ligand has two or more donor atoms and occupies two or more sites in a coordination sphere.

Thus, the term "metal chelating functionalities" refers to the groups that provides donor atoms. Usually, the functionalities are distanced from each other and hence the term "ligand arm" is used for each functionality.

The term "gel" is used for a separation matrix, which is in the form of a gel.

DETAILED DESCRIPTION OF THE INVENTION

Thus, in a first aspect, the present invention relates to a method of generating at least one polydentate metal chelating affinity ligand, which method comprises the steps of (a) providing at least one scaffold defined by the general formula (I)

wherein:
  $X_1$, $X_2$ and $X_3$ irrespective of each other are $sp^2$- or $sp^3$-hybridised carbon atoms or heteroatoms,
  $X_4$ is a nucleophile and
  m is an integer of 0–2;
(b) providing at least one polydentate metal chelating affinity ligand arm, optionally in a form wherein the metal chelating functionalities are protected, on each scaffold by derivatisation of the nucleophilic $X_4$ groups of said scaffolds while retaining the cyclic structure of the scaffold;
(c) ring-opening at the bond between the carbonyl and the sulphur of the derivatised scaffold by adding a reagent that adds one or more metal chelating affinity ligand arms to the scaffold; and, if required,
(d) deprotecting the functionalities of the ligand arm(s) provided in step (b).

The scaffold of step (a) can be provided as a solid or, preferably, in a solvent. In the most advantageous embodiment, in formula (I), $X_1$, $X_2$ and $X_3$ are carbon atoms. In alternative embodiments, one or more of $X_1$, $X_2$ and $X_3$ are heteroatoms, i.e. selected from the group comprised of oxygen, sulphur, nitrogen and/or silica, provided that said heteroatom does not interfere in the subsequent use of the ligands.

In formula (I), $X_4$ is any suitable nucleophilic group that enables derivatisation. Thus, in an illustrative embodiment, $X_4$ is selected from a group such as —OH, —SH or —$NH_2$. In an advantageous embodiment, $X_4$ is —$NH_2$.

As mentioned above, m can be any integer of 0–2, i.e. 0, 1, or 2. As appears from the method steps, the value of m will decide the number of atoms between the ligand arms and its attachment point to a base matrix when it is developed into a separation medium.

In an advantageous embodiment, in formula (I), m is 1 and the scaffold is homocysteine thiolactone. As the skilled person in this field will appreciate, homocysteine thiolactone can be used in pure or racemate form. Homocysteine thiolactone is commercially available, e.g. from Aldrich, catalogue no. H1, 580-2, and CAS no. 6038-19-3.

In step (b), the derivatisation is performed by adding a suitable derivatisation agent comprised of a first part, which is electrophilic and hence capable of reacting with $X_4$ of Formula (I), and a second part, which comprises a metal chelating functionality.

The first part of the derivatisation agent, i.e. electrophilic part, can be illustrated by C═C; C—Y, wherein Y represents for example a halogen, such as Br, I, Cl, or a mesylate, or a tosylate group; or an acid or an activated acid such as WC═O, wherein W is for example formed from N-hydrosuccinimide, pentafluorophenol, para-nitrophenol or isopropyl chloroformate.

In an advantageous embodiment, the derivatisation is provided by adding two derivatisation agents, each one of which comprises different or identical metal chelating functionalities, herein denoted $L_1$ and $L_2$. In this embodiment, the electrophilic parts of the agents are preferably of the same nature in order to facilitate the derivatisation. In an alternative embodiment, more than two different or identical metal chelating functionalities are introduced by derivatisation of $X_4$, preferably by use of two or more different steps, as is realised by the skilled person in this field. Accordingly, multiple functionalities are easily provided in the same, polydentate metal chelating affinity ligand.

The derivatisation agent(s) used in the present method can either comprise the metal chelating functionality in protected form, wherein the donor atoms are unavailable for reaction during the derivatisation of the scaffold, or in non-protected form. In the embodiment where the functionality is protected, said protecting group should be easy to remove in a subsequent step. Accordingly, the protecting group is either acid labile, such as an alkyl group, or base labile, such as a tert-butyl group. In one embodiment, the protecting group is a $CH_2CH_3$ group. Various metal chelating functionalities are known in this field, and can in principle be any electron-donating group. More specifically, the metal chelating functionalities used in the present method are selected from the group that consists of aromates, heterocyclic derivatives, such as pyridine, thiophene, furan and imidazole, acids, esters, ketones, amides, sulphones, sulphonamides, nitrile, carbon-carbon double and triple bonds.

In an illustrative embodiment, the derivatisation agent is a halogenated carboxylic acid ester, such as a halogenated carboxylic acid alkyl ester. As mentioned above, in a more specific embodiment, $X_4$ is $NH_2$. Methods for reacting an $NH_2$ group with a group carrying a halogen or another leaving group are well known in this field and are conveniently performed at ambient temperature in a solvent such as N,N-dimethylformamide (DMF). In one embodiment, in order to provide two metal chelating affinity ligand arms on each scaffold by the derivatisation, the derivatisation agent is used in a molar ratio of 2:1 to the scaffold. The skilled person can easily monitor the reaction and confirm the derivatisation obtained by a conventional method such as LC-MS. Thus, the present invention provides a less complex synthetic route to polydentate metal chelating affinity ligands than WO 01/81365. Due to the advantageous chemistry, the present method also results in a more homogenous product. The yields obtained according to the present method can be as high as 90%, and the starting materials are at present readily available to a reasonable cost.

In step (c), ring-opening is provided at the bond between the carbonyl and the sulphur of the derivatised scaffold by adding a reagent, which adds one or more metal chelating affinity ligand arms of the scaffold. Thus, the cyclic structure is opened up in order to provide one or more further metal chelating ligand arms.

The ring opening will also result in a handle available for subsequent coupling to a base matrix in the form of the thiophilic group, which due to its nucleophilic nature provides convenient coupling chemistry.

In an advantageous embodiment, the ring opening is hydrolysis by addition of alkali hydroxide, such as NaOH, in which case the carbonyl of the scaffold is transformed into a carboxylic group. However, as the skilled person in this field will understand, if the ring opening is performed with a different reagent, one or more different metal chelating functionalities can be introduced. In an alternative embodiment, the ring opening is aminolysis, in which case nitrogen carries one or more metal chelating functionalities. In this embodiment, the reagent is defined by the general formula II:

Formula 2 wherein $L_3$ and $L_4$ comprise metal chelating functionalities, which can be the same or different. Further, in one embodiment, said ligand arms $L_3$ and $L_4$ are the same as those provided in step (b) by the derivatisation.

Thus, as indicated above, in the embodiment where the metal chelating functionalities $L_1$ and $L_2$ were protected during the derivatisation step, a step of deprotection is preferably performed. In one embodiment, said deprotection is performed as a separate step that follows step (c), and can be achieved by adding a base or an acid, as indicated above. The chemistry useful for protection/deprotection of functionalities are well-known in this field, and the skilled person in this field can easily perform such steps.

In an especially advantageous embodiment of the present method, the deprotection is performed in the same step as the ring-opening. Accordingly, the great advantage of this embodiment is that polydentate metal chelating affinity ligands can be generated using a two step procedure. Consequently, this embodiment provides a less complex method than the prior art methods for the synthesis of polydentate metal chelating affinity ligands. In one embodiment, wherein the derivatisation agent comprises a base labile group, this step is provided by addition of sodium hydroxide. The hydrolysis is advantageously performed at ambient temperature for e.g. 1–2 hours. In fact, the present inventors have also shown that even though all the starting material can be converted within 90 minutes, an additional 48 hours does not give rise to any side products. Accordingly, the hydrolysis according to the invention results in a stable, homogenous and well-defined product. In an alternative embodiment, wherein the derivatisation agent comprises an acid labile group, in step (c), this step is provided by addition of an acid, such as HCl.

In a specific embodiment, in the present method, steps (a) and (b) have been performed earlier to provide a ready-derivatised scaffold Accordingly, the present invention also encompasses a method, wherein the carboxymethylation of the scaffold has been performed earlier.

In an advantageous embodiment, the product so obtained is coupled via its sulphur to a base matrix in order to produce a separation medium. Such a separation medium is useful for isolation of target substances, for analytical purposes etc. The base matrix used in the present method can be of any material suitable for the intended use.

Thus, in the case where the separation medium is intended for use in immobilised metal chelating affinity chromatography, the base matrix is commonly in beaded or monolithic form and made from natural polymers, e.g. agarose or dextran, or synthetic polymers, such as divinylbenzene or styrene. The base matrix can e.g. be in the form of a gel.

As regards natural polymers, suitable porous polymer beads thereof are either easily performed by the skilled person in this field according to standard methods, such as inverse suspension gelation (S Hjertén: Biochim Biophys Acta 79(2), 393–398 (1964) or spinning disk technique (see e.g. WO 88/07414 (Prometic Biosciences Inc)). Alternatively, natural polymer beads are obtained from commercial sources, such as Amersham Biosciences AB, Uppsala, Sweden. Illustrative tradenames of such useful natural polymer beads are e.g. of the kind known as Sepharose™ or Sephadex™.

As regards synthetic polymers, the base matrix is comprised of cross-linked synthetic polymers, such as styrene or styrene derivatives, divinylbenzene, acrylamides, acrylate esters, methacrylate esters, vinyl esters, vinyl amides etc. Such polymers are easily produced according to standard methods, see e.g. "Styrene based polymer supports developed by suspension polymerization" (R Arshady: Chimica e L'Industria 70(9), 70–75 (1988)). Alternatively, a commercially available product, such as Source™ (Amersham Biosciences AB, Uppsala, Sweden) can be surface-modified according to the invention.

In alternative embodiments, the base matrix can e.g. be a membrane, a filter, one or more chips, surfaces, capillaries etc.

In one embodiment, the reactive groups of the base matrix are allyl groups i.e. carbon-carbon double bonds. In one embodiment, a commercially available base matrix, which already exhibits allyl groups is used. In an alternative embodiment, the allyl groups are provided according to well known methods. Thus, in an illustrative embodiment, the present base matrix has been allylated by treatment with an epoxide carrying an allyl functionality at suitable temperatures and reaction times. One example of such a commonly used allyl-functional epoxide is allyl glycidyl ether (AGE). Accordingly, in a specific embodiment, in step (d), the sulphur group of the ligand is coupled to the base matrix via the activated allyl group of allyl glycidyl ether (AGE). In this embodiment, in the final product, the sulphur group will be attached to the base matrix by a spacer comprising ether groups and hydroxy groups, and the separation medium can be defined as base matrix —O—CH$_2$—CHOH—CH$_2$—O—CH$_2$—CHOH—CH$_2$—S— ligand.

In alternative embodiments, other well-known coupling techniques of thiol-containing ligands are used, such as opening of epoxide or radical addition to double bonds.

In a specific embodiment, said allyl groups are activated by bromination or alternatively, the coupling is a free radical reaction. The free radical used can be any suitable commercially available initiator, UV etc.

A second aspect of the present invention is a polydentate metal chelating affinity ligand or a separation medium comprising at least one, preferably a plurality of, polydentate metal chelating affinity ligands coupled to a base matrix, which medium has been generated by a method as described above. In a specific embodiment, the metal chelating affinity ligands are tridentate. Such a separation medium can then be charged with a suitable metal ion, such as Cu(II), Zn(II), Ni(II), Ca(II), Co(II), Mg(II), Fe(III), Al(III), Ga(III), Sc(III) etc, and used according to well known principles of IMAC, e.g. as outlined in the section "Background" above. In the most preferred embodiment, Ni$^{2+}$ is used.

In an advantageous embodiment, the present polydentate metal chelating affinity ligands are tridentate ligands are defined by the formula:

In a specific embodiment, the present separation medium, which comprises polydentate metal chelating affinity ligands coupled to a base matrix, is defined by the general formula:

wherein n is an integer of 2–4. In one embodiment, n=2. In this context, it is understood that if the base matrix is e.g. in the form of a particle, then a plurality of ligands will be coupled to each particle as described above.

A third aspect of the invention is the use of homocysteine thiolactone as a starting material in the preparation of polydentate metal chelating ligands. The invention also encompasses the use of a carboxymethylated scaffold such as homocysteine thiolactone in the preparation of polydentate metal chelating ligands. In the most advantageous embodiment, said use is as defined above. As mentioned above, homocysteine thiolactone is commercially available.

A further aspect of the present invention is a kit, which comprises a scaffold as defined by the general formula (I) above, which kit comprises said scaffold in a solid state together with instructions, preferably written, for use thereof in the manufacture of metal chelating affinity ligands or a separation medium comprising polydentate metal chelating affinity ligands coupled to a base matrix. In alternative embodiment, a kit according to the invention comprises any other form of the scaffold, such as a partly or fully derivatised scaffold, together with liquids and/or reagents suitable for performing the method according to the invention. In a specific embodiment, a kit is comprised of a scaffold reacted according to the present method except the deprotection, in which case the kit also comprises a suitable reagent for deprotection, such as a base or an acid, together with instructions for use.

The present invention also encompasses a chromatography column packed with a medium according to the invention. The column can be of any size, such as for large-scale production or lab-scale, or suitable for analytical purpose. The column can also be combined with separation medium and optionally liquids into a second kind of kit, which is also encompassed by the present invention. In one embodiment, the kit according to the invention comprises metal ions, such as $Ni^{2+}$ ions.

In addition, the present invention also relates to a process of separating a target substance from a liquid, which process comprises to provide a separation medium as defined above, to charge said medium with suitable metal ions to form chelates and to contact said medium with the liquid to adsorb the target substance thereon. In an advantageous embodiment, the process also comprises a step of eluting the target substance from the separation medium by adding a liquid that desorbs the target compound from the separation medium. In one embodiment, the elution is obtained by using a liquid that comprises a decreasing pH gradient or by applying a gradient giving an increasing imidazole concentration. The general principles of chromatography for separating a target substance as discussed above are well-known in this field, and the skilled person in this field can easily adopt the necessary parameters for use of the present process.

Finally, the present invention relates to a procedure of generating one or more diverse libraries of metal chelating affinity ligands for screening and optimising purposes. Thus, in this procedure, one arm carrying a dentate can be kept constant while other arms are selected in terms of optimal performance. As the skilled person will understand, for example one or more of the above-discussed $L_1$, $L_2$, $L_3$ and $L_4$ can be varied in order to identify the optimal form, and subsequently, once the optimised form has been identified, it is kept constant while other(s) are varied. Accordingly, the procedure of optimisation provides a tool to manufacture a separation medium comprising optimal, selected ligands.

Experimental Part

The following examples are provided for illustrative purposes only and should not be interpreted to limit the scope of the present invention as defined by the appended claims. All references given below or elsewhere in the present application are hereby included herein by reference.

Experimental $^1$H-NMR, $^{13}$C-NMR, CH-correlation, APT and cosy spectra were recorded in δ scale (ppm) with Bruker 300 MHz using TMS as reference. All spectra were recorded in $CDCl_3$ unless otherwise stated. TLC was carried out using Merck precoated silica gel $F_{254}$ plates. Ninhydrin or a mixture of Mo/Ce was used to visualise spots on TLC plates. LC-MS data were recorded using Hewlett Packard 1100 MSD electro spray. The flash column chromatographic purifications were carried out using Merck G-60 silica gel.

EXAMPLE 1

Carboxymethylation of Scaffold to Provide N,N-bis(ethyl-carboxymethyl ester)±homocysteine thiolactone In a dry 250 mL round-bottomed flask, the D/L homocysteine thiolactone (4.5 g, 29.22 mmol) was dissolved in 100 mL DMF. To this was added bromo-acetic acid ethyl ester (9.76 g, 58.44 mmol, 6.48 mL), KI (4.850 g, 29.22 mmol) and $NaHCO_3$ (14.727 g, 175 mmol). The reaction mixture was stirred at ambient temperature. The reaction was followed by TLC (toluene:ethyl acetate 3:1) and LC-MS data. The reaction was completed after 3.5 h.

The desired product has a $R_f$=0.35 (toluene:ethyl acetate 3:1). The solvent was evaporated, the resulting solid redissolved in $CHCl_3$, extracted with $H_2O \times 2$. The organic phase was finally dried over $Na_2SO_4$, filtered and evaporated. The product was purified on flash column chromatography (toluene:ethyl acetate 3:1).

Yield: 7.636 g (26.422 mmol), 90%. $^1$H-NMR: δ 1.52 (t, 6H, C$\underline{H}_3$—$CH_2$—O—), δ 2.05–2.56 (m, 2H, —S—C$\underline{H}_2$—$CH_2$—CH—C═O), δ 3.25 (m, 2H, —S—$CH_2$—C$\underline{H}_2$—CH—C═O), δ 3.52 (s, 4H, —N—C$\underline{H}_2$—N—C$\underline{H}_2$—), δ 3.65 (dd, 1H, S—$CH_2$—$CH_2$—C$\underline{H}$—C═O), δ 4.24 (m, 4H, $CH_3$—C$\underline{H}_2$—O—); $^{13}$C-NMR: δ 14.71 ($\underline{C}H_3$—$CH_2$—O—), δ 27.42 (S—$\underline{C}H_2$—$CH_2$—CH—C═O), δ 29.68 (S—$CH_2$—$\underline{C}H_2$—CH—C═O), δ 54.01 ($CH_3$—$\underline{C}H_2$—O—), δ 60.99 (—N—$\underline{C}H_2$—N—$\underline{C}H_2$), δ 67.15 (—S—$CH_2$—$CH_2$—$\underline{C}H$—C═O), δ 170.94 (O═$\underline{C}$—CH2-N—CH2-$\underline{C}$═O), δ 207.20 (—S—$CH_2$—$CH_2$—CH—$\underline{C}$═O). LC-MS: $M^+$ 290.

EXAMPLE 2

Hydrolysis to Provide N,N-bis(carboxymethyl)±homocysteine and Stability Test

N,N-bis(ethyl carboxymethyl ester)+/−homocysteine thiolactone (50 mg, 0.173 mmol) prepared as described in example 1 above, was dissolved in 1 mL 1M NaOH. In a 100 mL round-bottomed flask. The reaction mixture was stirred at ambient temperature for 100 minutes. The reaction was followed to completion until no starting material was visible according to LC-MS.

Stability test: After complete hydrolysis, the above reaction mixture was diluted to 5 mL with $H_2O$. The pH was adjusted to 12.5 and the reaction mixture was heated at 50° C. with stirring. A 50 μL sample was withdrawn from the mixture with 1 h intervals for four hours. Each 50 μL sample was then mixed with 1 mL MeOH for the LC-MS analysis. After this step, the reaction mixture was allowed to stand overnight and finally a 50 μL sample was withdrawn for the LC-MS analysis as described above. No decomposition was observed during the time of the experiment.

The crude product was freeze-dried.

$^1$H-NMR (D$_2$O): δ 1.52 (m, 2H, —CH—CH$_2$—CH$_2$—SH), δ 2.24 (m, 2H, —CH—CH$_2$—CH$_2$—SH), δ 3.20 (m, 5H, O=C—CH$_2$—N—CH—); $^{13}$C-NMR (D$_2$O): δ 22.34 (—CH—CH$_2$—CH$_2$—SH), δ 35.39 (—CH—CH$_2$—CH$_2$—SH), δ 57.33 (O=C—CH$_2$—N—CH$_2$—), δ 67.30 (—CH—CH$_2$—CH$_2$—SH), δ 180.55 (O=C—CH$_2$—N—CH$_2$—C=O), δ 181.84 (—N—CH—C=O); LC-MS: M$^+$ 252.

EXAMPLE 3

Coupling of the Product Obtained from Example 2 to Allylated Agarose Using AGE 10 ml Sepharose™ HP-allyl (Amersham Biosciences, Uppsala, Sweden) (44 μmol/ml gel) was stirred in 20 ml distilled water with 1 g NaOAc. Br$_2$ aq. saturated was added until that a persisting yellow colour is formed. Sodium formate was then added until the yellow colour has disappeared. The gel was then washed with distilled water. N,N-bis(ethyl carboxymethyl ester)+/−homocysteine thiolactone (102 mg) was stirred in 2 ml 1M NaOH at room temperature for 2 hours. 5 ml distilled water and 3 ml 1M NaHCO$_3$ was added, and the pH was adjusted to 11.0 with 2M NaOH.

The ligand solution was then added to the drained gel in a vial, which was capped.

The vial was shaken at 50° C. for 16 h, then the gel was washed with distilled water on a glass filter funnel.

EXAMPLE 4

Purification of Maltose Binding Protein with (His)$_6$-Tail (MBP-His) Using an IMAC Separation Medium Generated According to the Invention and Metal Leakage Test Materials and Methods:

Extract with MBP-His

C-terminally hexaHis-tailed Maltose Binding Protein, MBP-His, theoretical Mr and pI was 43 781 and 5.4:

Fermentation of an *E. coli* clone expressing MBP-His and cell homogenisation was performed according to a standard procedure. The concentration of MBP-His in this extract was estimated to approximately 1.9 mg/ml.

IMAC A-Buffer:

For one litre: (one PBS tablet to 1000 ml water is specified to give 10 mM Na-phosphate, 140 mM NaCl and 3 mM KCl, pH 7.4.) Two PBS tablets were dissolved in water, NaCl was added from 5 M stock to give an extra 720 mM (thus finally 140+140+720 mM=1 M), pH adjusted to 7.4 with NaOH and final volume to 1000 ml. (Buffer also contains 6 mM KCl).

Elution Buffer (IMAC B-Buffer):

Prepared in the same way as IMAC A-buffer, but also imidazole was added to 500 mM (from 2.0 M stock of imidazole-HCl, pH 7.4) before final adjustment of pH and volume.

Ni$^{2+}$-Sulphate Solution: 100 mM in water. Filter 0.2 um. pH≈4.6.

Sample buffer and running conditions according to Instructions for ExcelGel™ (Amersham Biosciences, Uppsala, Sweden).

Gels: ExcelGel™ SDS, gradient 8–18%.

Sample prep: Samples were mixed 1+1 with 2× sample buffer (for purifications with large amounts of target protein) or 1 volume sample+⅓ volume 4× sample buffer (purifications with small amounts of target protein). (4× sample buffer=100 mM Tris-HAc pH 7.5, 2% SDS.) Heating at 95° C. for 3–5 minutes.

Sample application: IEF sample application pieces (5×10 mm filter paper pieces, # 80-1129-46 (Amersham Biosciences, Uppsala, Sweden) were used. Up to 30–32 paper pieces were positioned with their short sides towards the running direction. 20 μl sample cocktail was applied to each piece. The pieces were left on the gel during the whole electrophoresis.

Electrophoresis: In a Multiphor™ II (Amersham Biosciences, Uppsala, Sweden) apparatus at 15° C. (circulating cooling bath). EPS 3500 Power Supply. Limiting settings: 600 V, 50 mA, 30 W.

Staining: In 0.1% Coomassie R 350 dissolved in 30% MeOH, 10% HAc. Destaining in 25% EtOH, 8% HAc.

Chromatography: The media was packed in HR 5/5 columns (Amersham Biosciences, Uppsala, Sweden) to a bed height of 5 cm=1.0 ml bed. The media was charged with Ni$^{2+}$ prior to use by pumping the Ni-sulphate solution onto the column (5 column volumes), followed by water and by equilibration with binding buffer (=IMAC A-buffer) with 5 mM imidazole added). A short blank run was performed by applying elution buffer, again followed by equilibration with binding buffer.

The *E. Coli* extract with MBP-His, 1.0 M NaCl, 5 mM imidazole and 1 mM PMSF (freshly added) was clarified by centrifugation and by 0.45 um filtration. The required volume was then introduced into a Superloop™ (Amersham Biosciences, Uppsala, Sweden) through a 0.2 um filter shortly prior to IMAC start. 3 ml was then applied to the column. After extensive washing with binding buffer, a 20-ml linear gradient was run (to 40% Elution buffer=200 mM imidazole) using a ÄKTA™ Explorer 10 system (Amersham Biosciences, Uppsala, Sweden). Finally, a 5-ml push with 100% Elution buffer (500 mM imidazole) was applied. All steps were at 1.0 ml/min.

EXAMPLE 5

Figure 1:
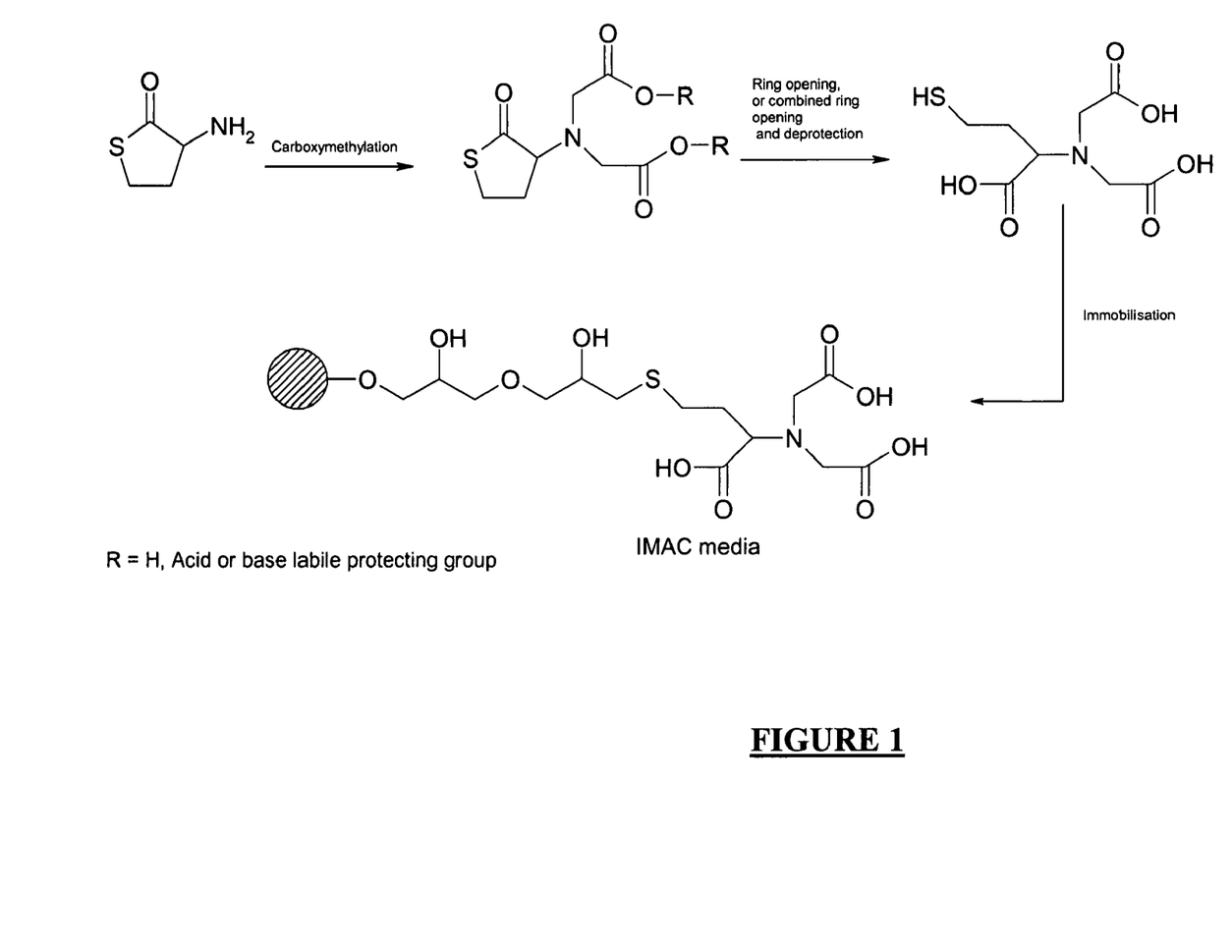
FIG. 1 provides a schematic illustration of the general route to produce a separation medium that comprises polydentate metal chelating affinity chromatography ligands according to the invention. The first step corresponds to step (b) of the present method, i.e. a derivatisation, the second step is a hydrolysis to open up the ring of the derivatised scaffold and the last step is immobilisation i.e. coupling of the ligand so produced to a base matrix. As appears from the above, the second step is advantageously a combined ring-opening and deprotection.
Figure 2:
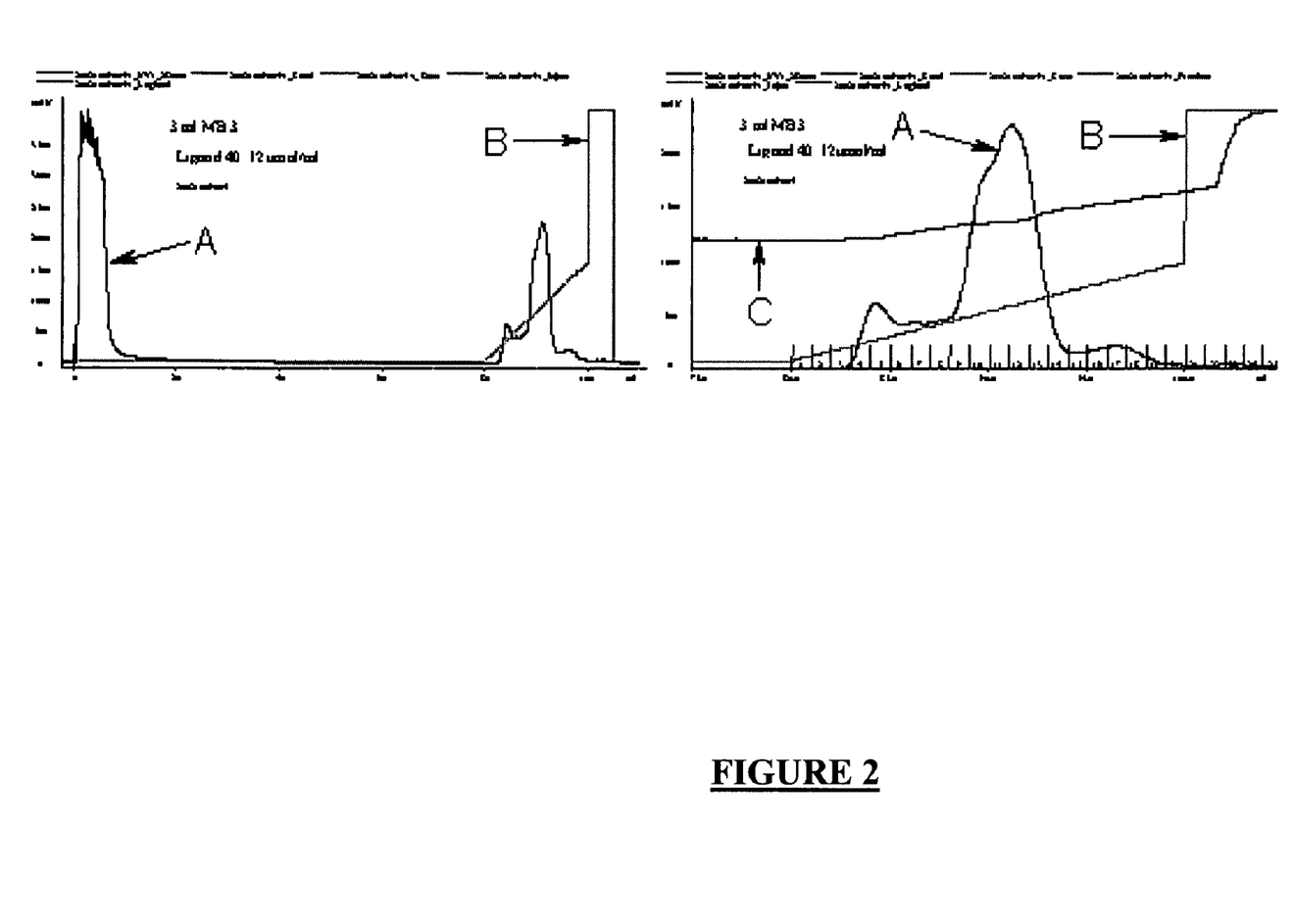
Figure 3:
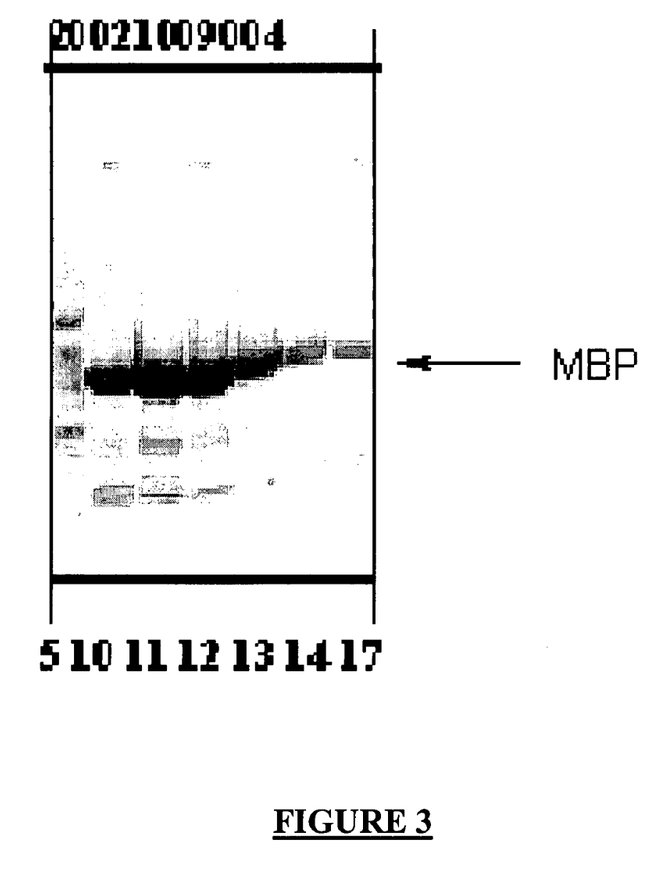
FIG. 3 shows SDS-PAGE analyses of fractions from IMAC purification of MBP-His. Fraction numbering as in FIG. 2 chromatogram.
Figure 4:
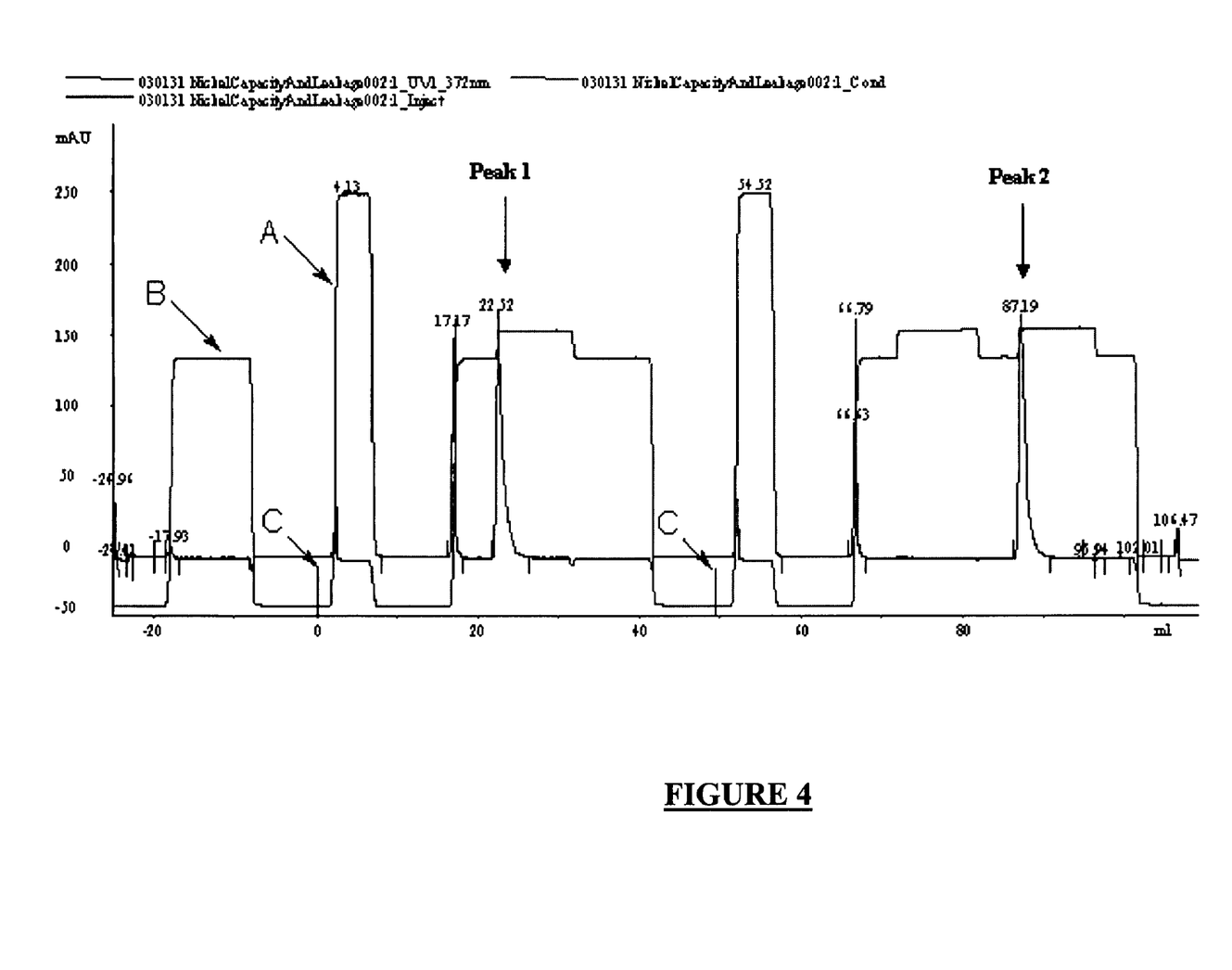
FIG. 4 shows a test chromatogram, wherein UV 372 nm=A, Conductivity=B, Injection=C. The nickel-binding capacity of this prototype was determined to 16 $\mu$mol Ni/ml and the metal leakage to 4% (see Example 5).

Determination of Nickel-Binding Capacity and Metal-Leakage at pH 4.0 Nickel Binding Capacity The nickel (Ni$^{2+}$) binding capacity of a separation medium according to the invention was determined chromatographically using an ÄKTA™ Explorer 10 system (Amersham Biosciences, Uppsala, Sweden) equipped with a UV/V is DAD detector. The test was performed on gel to which N,N-bis(carboxymethyl)+/−homocysteine had been coupled according to earlier description, and packed in 1-ml HR5/5 columns (FIG. 4). This result was compared with the ligand density present on the gel as determined by elemental analysis (nitrogen analysis, each ligand containing one nitrogen atom).

Figure 5:
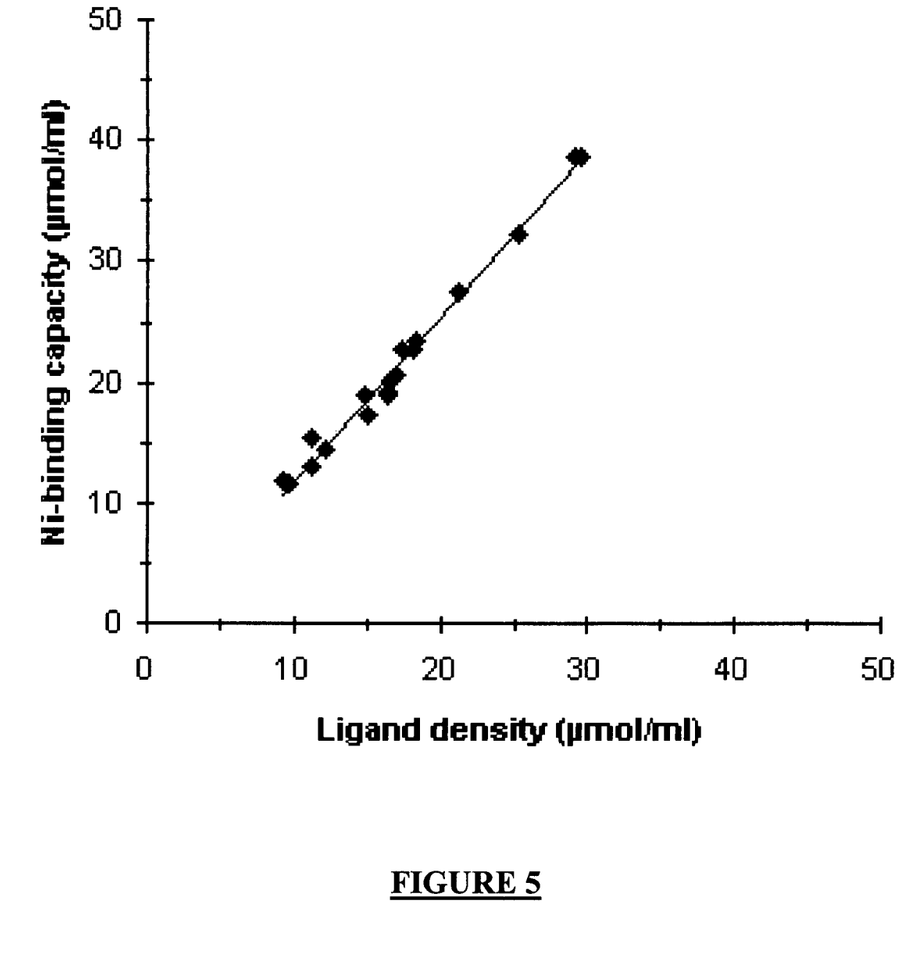
FIG. 5 shows the results of the nickel capacity test performed on a separation medium according to the invention as described in Example 5.

The correlation between nickel-binding capacity and ligand density was considered to be very good, i.e. one ligand is carrying one metal ion. Typical results are shown in FIG. 5.

Method Description

A $NiSO_4$ solution was injected to load the gel with $Ni^{2+}$ ions. Excess metal was removed by washing with water and phosphate buffer (20 mM $PO_4$, 500 mM NaCl, pH 7.4). The nickel ions bound to the gel were eluted with EDTA, which is a very strong chelator and efficiently strips the metal ions from the gel. The peak area of the green coloured Ni-EDTA complex eluted was measured at 372 nm. A linear calibration curve was established from solutions with different concentrations of Ni-EDTA and was used for quantification. The nickel-binding capacity (FIG. 4, peak 1) was given as μmol Ni/ml packed gel.

Metal Leakage

A metal leakage test was performed to test the stability of the ligand-nickel complex. The nickel-loaded gel was then washed with acetate buffer, pH 4.0. before determining the Ni-content on the gel (FIG. 4).

The metal leakage was considered to be very low for all tested gels prepared according to the present invention; typically the leakage was 4%.

Leakage of nickel ions was tested analogously to the nickel-binding capacity. However, before eluting nickel ions with EDTA, the gel was washed with ten column volumes of acetate buffer, 100 mM, pH 4.0. The leakage was given as % of the binding capacity and was determined as the difference between the nickel-binding capacity and the amount eluted after washing with pH 4 (FIG. 4, peak 2) according to the formula: $(area_{Peak\ 2} - area_{Peak\ 1})/area_{Peak\ 1}$.

FIG. 5 shows the results of the nickel-capacity test performed on a separation medium according to the invention as described in Example 5. More specifically, the X axis shows the ligand density while the Y axis shows the nickel-binding. It appears clearly that the nickel-binding capacity increases linearly with the ligand density and that the slope is close to one.

The above mentioned embodiments are intended to illustrate the present invention and are not intended to limit the scope of protection claimed by the following claims.

What is claimed is:

1. A method of generating at least one polydentate metal chelating affinity ligand, which method comprises the steps of
   (a) providing at least one scaffold defined by a ring of the general formula (I)

wherein
$X_1$, $X_2$ and $X_3$ irrespective of each other are $sp^2$- or $sp^3$-hybridised carbon atoms or heteroatoms,
$X_4$ is a nucleophile and m is an integer of 0–2;
   (b) providing at least one polydentate metal chelating affinity ligand arm on each scaffold by derivatisation of the nucleophilic $X_4$ groups of said scaffolds while retaining the cyclic structure of the scaffold; and
   (c) opening the ring at a bond between the carbonyl and the sulphur of the derivatised scaffold by adding a reagent that adds one or more metal chelating affinity ligand arms to the scaffold.

2. The method of claim 1, wherein in formula (I), $X_1$, $X_2$ and $X_3$ are carbon atoms.

3. The method of claim 1, wherein in formula (I), $X_4$ is —$NH_2$.

4. The method of claim 1, wherein in formula (I), m is 1 and the scaffold is homocysteine thiolactone.

5. The method of claim 1, wherein in step (b), the derivatisation is provided by adding at least one derivatisation agent comprised of one part, which is electrophilic and hence capable of reacting with $X_4$ in Formula (I), and a second part, which is a metal chelating affinity ligand.

6. The method of claim 5, wherein the derivatisation is provided by adding two derivatisation agents, which comprise two different or identical metal chelating functionalities.

7. The method of claim 5, wherein said at least one derivatisation agent is a halogenated, protected ester.

8. The method of claim 7, wherein said at least one derivatisation agent is bromo-acetic acid ethyl ester.

9. The method of claim 1, wherein in step (c), ring-opening is hydrolysis provided by adding a base.

10. The method of claim 1, wherein the metal chelating affinity ligand arms are protected in step (b).

11. The method of claim 10, further comprising the steps of deprotecting the chelating affinity ligand arms after step (c) and coupling the resultant compound via its thiol group to a base matrix in order to produce a separation medium.

12. The method of claim 11, wherein the thiol group is coupled to allyl groups of the base matrix.

13. The method of claim 11, further comprising a step of allylating the base matrix to provide reactive groups to permit said coupling.

14. The method of claim 11, wherein the thiol group of the ligand is coupled to the base matrix via an allyl group of allyl glycidyl ether (AGE).

15. The method of claim 11, further comprising a step of activating the reactive groups of the base matrix.

16. The method of claim 15, wherein the activating is performed by bromination.

* * * * *